United States Patent
Scherer et al.

(10) Patent No.: US 8,736,842 B2
(45) Date of Patent: May 27, 2014

(54) ACTUATION AND EVALUATION CIRCUIT, MEASURING DEVICE AND METHOD FOR MEASURING THE CONCENTRATION OF A GAS

(75) Inventors: Helmut Scherer, Höchberg (DE); Dieter Schrader, Höchberg (DE); Stefan Menninger, Höchberg (DE)

(73) Assignee: Carefusion Germany 234 GmbH, Hochberg (DE)

( * ) Notice: Subject to any disclaimer, the term of this patent is extended or adjusted under 35 U.S.C. 154(b) by 120 days.

(21) Appl. No.: 13/266,610

(22) PCT Filed: Apr. 14, 2010

(86) PCT No.: PCT/DE2010/050018
§ 371 (c)(1),
(2), (4) Date: Feb. 15, 2012

(87) PCT Pub. No.: WO2010/124685
PCT Pub. Date: Nov. 4, 2010

(65) Prior Publication Data
US 2012/0281220 A1     Nov. 8, 2012

(30) Foreign Application Priority Data

Apr. 27, 2009  (DE) .......................... 10 2009 018 620

(51) Int. Cl.
| | | |
|---|---|---|
| *G01N 21/00* | (2006.01) | |
| *G01J 1/00* | (2006.01) | |
| *G01N 21/39* | (2006.01) | |
| *G01N 21/85* | (2006.01) | |
| *G01J 1/42* | (2006.01) | |

(52) U.S. Cl.
CPC ............ *G01N 21/39* (2013.01); *G01N 21/8507* (2013.01); *G01J 1/4257* (2013.01); *G01J 1/42* (2013.01)
USPC ............ 356/437; 356/436; 356/213; 356/218

(58) Field of Classification Search
CPC ....................................................... G01N 21/00
USPC ................................................. 356/432–437
See application file for complete search history.

(56) References Cited

U.S. PATENT DOCUMENTS

| 5,184,017 A | 2/1993 | Tury et al. |
| 5,202,560 A * | 4/1993 | Koch et al. ..................... 250/238 |
| 5,757,976 A * | 5/1998 | Shu ............................. 382/252 |

(Continued)

FOREIGN PATENT DOCUMENTS

| DE | 3627876 C2 | 2/1988 |
| DE | 19962178 A1 | 6/2001 |
| DE | 102005055938 A1 | 6/2006 |
| EP | 1111372 A1 | 6/2001 |

(Continued)

OTHER PUBLICATIONS

Wavelength turning and spectral properties of distributed feedback diode lasers with a short external optical cavity Christian K. Laue, Ralph Knappe, Klaus-Jochen Boller, and Richard Wallenstein Jun. 20, 2001/ vol. 40, No. 18/ Applied Optics.

*Primary Examiner* — Michael P Stafira
(74) *Attorney, Agent, or Firm* — King & Schickli, PLLC

(57) ABSTRACT

The invention relates to an actuation and evaluation circuit for a laser diode (1) and a photodiode (3) for determining the concentration of a gas. The laser diode can generate light in the range of an absorption line of the gas. The circuit comprises a driver (10, 11, 12, 13) for generating a driving signal (17) for the laser diode (1), an assembly (8, 9) for generating a reference signal (20), and a subtractor (5) for subtracting the reference signal (20) from the signal (21) supplied by the photodiode. The invention further relates to a measuring device for determining the concentration of a gas by means of such an actuation and evaluation circuit. Finally, the invention relates to a corresponding method.

12 Claims, 1 Drawing Sheet

(56) References Cited

U.S. PATENT DOCUMENTS

| | | |
|---|---|---|
| 5,818,578 A | 10/1998 | Inman et al. |
| 6,091,504 A | 7/2000 | Walker et al. |
| 6,150,661 A | 11/2000 | McCaul et al. |
| 2006/0044562 A1* | 3/2006 | Hagene et al. ............... 356/437 |

FOREIGN PATENT DOCUMENTS

| | | |
|---|---|---|
| EP | 1475618 A1 | 11/2004 |
| EP | 1772098 A1 | 4/2007 |
| GB | 2412728 A | 10/2005 |
| WO | 2008079032 A2 | 7/2008 |

* cited by examiner

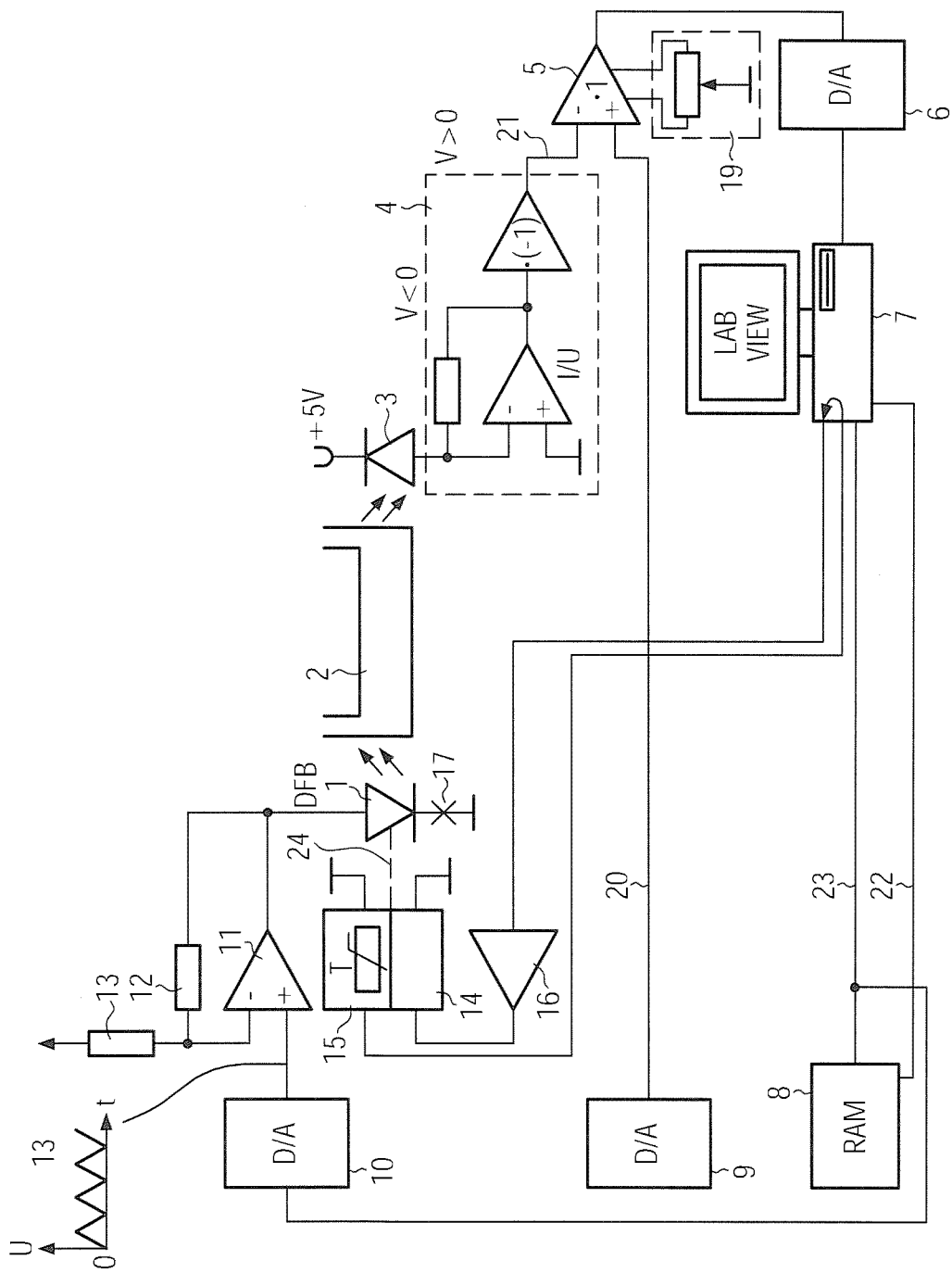

ACTUATION AND EVALUATION CIRCUIT, MEASURING DEVICE AND METHOD FOR MEASURING THE CONCENTRATION OF A GAS

This application is the national stage of PCT/DE2010/050018, filed Apr. 14, 2010, which claims priority from German Patent Application No. 102009018620.4, filed Apr. 27, 2009, the full disclosures of which are incorporated herein by reference.

FIELD OF THE INVENTION

The invention relates to the field of actuation and evaluation circuits of the type defined in the preamble of patent claim 1, to measuring devices comprising such a circuit as well as to a method of the type defined in the preamble of patent claim 9.

The invention relates to the determination of the concentration of one or more gases by means of a transmission measurement. Specifically, the absorption of an absorption line of the gas or any gas is determined by means of the transmission measurement, and conclusions are drawn therefrom on the concentration of the gas or any one of the gases.

BACKGROUND OF THE INVENTION

Various measurement arrangements and measurement methods are known in the prior art, in which the concentration of the gas in a measuring volume is deduced from the absorption of an absorption line of a gas. Basically, these methods may also be used for analyzing gas mixtures. In this case, at least one measurement in an absorption line has to be carried out for each gas. Ideally, each absorption line should be in another range of the light spectrum. Below, we shall confine ourselves to determining the concentration of a single gas, e.g. $O_2$, $CO_2$, He or $N_2$ in air. With respect to gases which naturally occur to a considerable extent in natural air, that is $O_2$ and $N_2$, possibly also $CO_2$, the term concentration refers to the absolutely present amount of gas. Measuring methods used in medical engineering, in which the concentration of the above-mentioned gases is measured, are described inter alia in EP 1772098 A1 (VI11P).

In order to determine the absorption it is possible, for example, to introduce chopped or pulsed light with a highest possible portion in the range of an absorption line of the gas to be measured into a measuring volume by irradiation. By the absorption the gas in the measuring volume is periodically heated, so that initially temperature differences are created, pressure differences as a result thereof, and thus sound. The louder the sound, the higher is the concentration of the gas.

In other measuring methods the light is generated by a broadband light source, and the light transmitted through a measuring volume is measured by a photodiode. This configuration involves the problem that also the light next to the absorption line contributes to the quantum noise in the photodiode. As is known, the quantum noise increases proportionally to the root of the photocurrent. Apart from cross sensitivities with respect to other gases, such a configuration works, therefore, only with an optical filter, which limits the spectral range of the light to the range around an absorption line or an absorption band. In other circumstances the relative alteration of the photodiode current by the absorption is too small. This methods works the better, the less light is permitted by the optical filter to pass through next to the absorption line.

Recently, tunable semiconductor lasers were brought on the market, whose line width is clearly more narrow than the typical absorption line of a gas of interest of about 1 nm, and whose laser line can be varied by more than 1 nm by the intensity of the current flowing through the semiconductor laser. The alteration of the laser line is particularly due to an alteration of the refraction index as a result of a higher temperature of the semiconductor crystal. The influence of the alteration of the refraction index on the wavelength is stronger by about 20 times as compared to the alteration of the volume expansion of the semiconductor crystal at the same temperature change. Such semiconductor lasers are used for analyses in space aviation, especially for expeditions to other planets. In order to determine the absorption of the gas to be measured, the strongly non-linear characteristic of the semiconductor laser has to be subtracted out from the measurement points by a fit.

SUMMARY OF THE INVENTION

It is the object of the invention to provide an actuation and evaluation circuit as well as a corresponding method which is adapted for terrestrial conditions.

This object is achieved with the teaching of the independent claims.

Specifically, the object is achieved by subtracting a reference signal from the transmission signal supplied by a photodiode. By this, the non-linear characteristic of the semiconductor laser is compensated in a surprisingly simple manner. The possibly slightly greater weight is immaterial on earth.

Preferred embodiments of the invention are defined in the dependent claims.

Advantageously, a digital memory for storing a characteristic may be used.

Due to the good dynamics and simple construction of analog subtractors, the subtraction of the transmission signal from the reference signal is carried out in an analog manner. The digital-analog converter required to this end is less expensive than a corresponding analog-digital converter and, therefore, does not constitute any substantial argument against an analog subtraction.

An analog addition of an offset to the signal supplied by a second digital-analog converter for generating an analog signal in order to actuate the semiconductor laser keeps the dynamic range small and, thus, the cost for the second digital-analog converter low.

Advantageously, the address lines of the digital memory for storing a characteristic can be connected to the digital inputs of the second digital-analog converter, which reduces the complexity of the required control signals.

A symmetric sawtooth signal at the digital inputs of the second digital-analog converter allows a uniform heating and cooling of the semiconductor crystal of the laser and, thus, a uniform passing through of the absorption line of the gas to be measured.

By the integration of the output signal of the subtractor either over a period of the driving signal or the period from a minimum to a maximum of the driving signal or the period from a maximum to a minimum of the driving signal one obtains the surface area underneath the absorption line of the gas to be measured in a simple manner, and thus a measure for the concentration of the gas to be measured.

BRIEF DESCRIPTION OF THE DRAWING FIGURE

A preferred embodiment of the invention will be explained in more detail below with reference to the accompanying drawing. In the drawing:

FIG. 1 shows a schematic circuit diagram of the actuation and evaluation circuit according to the invention.

DETAILED DESCRIPTION OF THE INVENTION

FIG. 1 shows a schematic circuit diagram of the actuation and evaluation circuit according to the invention. The gas to be measured is located, possibly together with other gases, in a cuvette 2. Pneumatic connections at the cuvette allow a gas exchange in the cuvette 2. Light in the range of an absorption line of the gas to be measured is generated by a DFB semiconductor laser 1 (DFB: distributed feedback). Transmitted light is converted by a photodiode 3 into an electric current. A current-voltage converter 4 converts the current supplied by the photodiode 3 into a voltage. Experts are aware that a current-voltage converter 4 can comprise an operation amplifier fed back by a resistor and, where necessary, an inverter. The output signal of the current-voltage converter 4 is designated as transmission signal 21.

A subtractor 5 subtracts the transmission signal 21 from a reference signal 20. The subtractor supplies a difference signal, which is supplied to an analog-digital converter 6. The analog-digital converter 6 scans at a frequency of 5 to 10 kHz. The subtractor 5 may include an offset compensation 19 so as to optimally use the dynamic range of the analog-digital converter 6 and keep the required resolution and, thus, the cost for the analog-digital converter 6 at a minimum. The digital output signal of the analog-digital converter 6 may be supplied to a computer 7 or a microprocessor.

The computer 7 or microprocessor generates a digital control signal which is supplied both to the address inputs of the memory 8 and the digital-analog converter 10. The control signal has, for example, a periodic, specifically symmetric, sawtooth-shaped, time-dependent curve and a frequency of 5 Hz. The digital-analog converter 10 generates from the digital control signal an analog control signal, to which the difference amplifier 11 adds a first offset in interaction with resistors 12 and 13.

This first offset roughly tunes the semiconductor laser 1 to the absorption line to be measured, so that the semiconductor laser 1 generates at the minimum output voltage of the digital-analog converter 10 light at a frequency above the absorption line, and at a maximum output voltage of the digital-analog converter 10 light at a frequency below the absorption line. Also, the first offset can be adapted to generate in the case of a control signal equal to the arithmetic mean of the minimum and maximum control signal laser light whose frequency corresponds to the maximum of the absorption line. In this way the dynamics of the digital-analog converter 10 is optimally used. In addition, the difference amplifier 11 also assumes the function of a power amplifier, so that in particular sufficient current for the semiconductor laser 1 is made available. The current through the semiconductor laser is also referred to as driving signal 17.

If the current through the semiconductor laser 1 changes, not only the frequency of the emitted light is altered, which is desirable in this application, but also the intensity of the emitted light is altered, which has to be compensated for in some way. According to the invention this compensation is accomplished by memory 8. Suitable values are stored in the memory cells of memory 8, which correspond to the transmission signal 21 in case of a zero concentration of the gas to be measured, so that the difference signal at the output of the subtractor 5 is preferably zero.

Zero concentration refers to the concentration which the gas to be measured has in the ambient air. Especially for the gases $N_2$ and $O_2$ this concentration is non-zero. In case of $CO_2$, too, it may be necessary to take the portion of 0.04% in the air into account. This definition of the zero concentration allows a simple calibration of the device in the ambient air. Alternatively, also a gas bottle with a gas mixture of a known composition or a calibration cuvette having an enclosed test gas may be used for the calibration.

The semiconductor laser 1 (Manufacturer: Nanoplus GmbH, Serial Number 350/10-23) is fixed in a TO5 casing by means of a mount. The mount comprises a Peltier element 14 and a thermistor 15. Therefore, the Peltier element 14 and the casing of the semiconductor 1 are in thermal contact 24, which is illustrated in the figure as a broken line. The Peltier element is actuated by a driver 16. In the embodiment illustrated in FIG. 1 the computer 7 closes a feedback loop from the thermistor 15 via the driver 16 to the Peltier element 14, so that the temperature of the mount is kept largely constant and, thus, is not influenced especially by fluctuations in the ambient temperature. The temperature of the semiconductor laser 1 itself deviates more or less from the temperature of the mount in dependence on the height of the control signal.

Basically, any conventional memory module may be used as memory 8. However, a pure ROM (Read Only Memory) is not practical because it does not permit a recalibration. Well suited are writeable, non-volatile memories such as EEPROMs (Electrically Erasable Programmable ROM). In the embodiment shown in FIG. 1 even a RAM (Random Access Memory) is used, into which the memory cells are written anew via data line 22 at each switch-on process (boot-up). Typically, a computer 7 comprises a non-volatile memory such as a hard disk. The data line 22 allows a recalibration.

The evaluation of the difference signal is accomplished by the integration over the n-time passing through of an absorption line, whereby n is a natural number (1, 2, 3, . . . ) and an integral signal is obtained. Each falling and each rising edge of the symmetric sawtooth-shaped control signal corresponds to a passing through of the absorption line. That is, the integration is made over a period that lasts one or more rising and/or falling edges of the control signal. This may be accomplished in an analog manner by an integrator, or digitally by adding up the samples supplied by the analog-digital converter 6. The latter is realized in the embodiment shown in FIG. 1. By means of the integration or adding up the noise is brought down to an acceptable level. The integral signal has a good proportionality to the gas concentration, more specifically to the deviation of the gas concentration from the zero concentration.

Due to the limited resolution of the digital-analog converters 9 and 10 the difference signal will fluctuate at least between two values which correspond to ±½ Bit of the resolution of the digital-analog converters 9 and 10. The two values may be dependent on the height of the digital control signal due to the non-linear characteristic of the semiconductor laser 1. The accuracy, with the parameters being the same, can be improved by calculating the values stored in memory 8 in such a way that the integral signal also fluctuates only by a value, if possible, that corresponds to ±½ Bit of the resolution of the digital-analog converters 9 and 10. At this point one need not be modest and can use the range of the control signal in which ±½ Bit lead to a particularly small difference signal. For such an exact calibration it will be necessary to pass through the absorption line clearly more often as compared to a normal measurement in order to further reduce the noise and increase the reproducibility.

So far, the embodiment illustrated in FIG. 1 has only been used for measuring the $O_2$ concentration at a wavelength of 760.26 nm. It is envisaged to determine the concentrations of the following gases: CO, $O_2$, $CO_2$, $C_2H_2$, $CH_4$, He, $SF_6$ and NO.

In the foregoing, the invention was explained in more detail by means of preferred embodiments. Those skilled in the art will appreciate, however, that various alterations and modifications may be made without departing from the spirit of the invention. Therefore, the scope of protection is defined by the following claims and their equivalents.

LIST OF REFERENCE NUMBERS

1 DFB laser diode
2 cuvette
3 photodiode
4 current-voltage converter
5 subtractor
6 analog-digital converter
7 computer
8 memory
9 digital-analog converter
10 digital-analog converter
11 difference amplifier
12, 13 resistor
14 Peltier element
15 thermistor
16 driver
17 driving signal
19 offset compensation
20 reference signal
21 transmission signal (of photodiode)
22 data line
23 control signal
24 thermal contact

The invention claimed is:

1. Actuation and evaluation circuit for a laser diode and a photodiode for determining the concentration of a gas, the laser diode being suited to generate light in the range of an absorption line of the gas, comprising:
a driver for generating a driving signal for the laser diode;
the driver comprising a first digital-analog converter for analog-converting a digital control signal for generating said driving signal; and
an assembly for generating a reference signal;
the assembly comprising:
a digital memory for storing a characteristic of the laser diode; and
a second digital-analog converter electrically connected to the digital memory in such a way that the second digital-analog converter receives digital values read out from the digital memory and the second digital-analog converter converts the received values into the reference signal; said actuation and evaluation circuit further comprising:
a subtractor for subtracting the reference signal from the signal supplied by the photodiode.

2. Circuit according to claim 1, characterized in that the driver further comprises an adder electrically connected to the first digital-analog converter in such a way that the analog output signal of the first digital-analog converter is supplied to the adder and the adder can add a first constant offset to the analog output signal of the first digital-analog converter, wherein the output of the adder is connectable to the laser diode.

3. Circuit according to claim 2, characterized in that the address lines of the digital memory are electrically connected to the digital inputs of the first digital-analog converter.

4. Circuit according to claim 2, characterized in that a microprocessor is connected to the digital inputs of the first digital-analog converter and can apply a triangle signal to the same.

5. Circuit according to claim 1, further characterized by an integrator electrically connected to the output of the subtractor, the integrator being suited to integrate the output signal of the subtractor either over a period of the driving signal or the period from a minimum to a maximum of the driving signal or the period from a maximum to a minimum of the driving signal.

6. Measuring device for determining the concentration of a gas, comprising:
a cuvette containing the gas;
a tunable laser diode for generating light in the range of an absorption line of the gas;
a photodiode for detecting the light transmitted through the gas in the cuvette; and
an actuation and evaluation circuit comprising:
a driver being electrically connected to the laser diode, the driver for generating a driving signal for the laser diode;
the driver comprising a first digital-analog converter for analog-converting a digital control signal for generating said driving signal; and
an assembly for generating a reference signal; the assembly comprising:
a digital memory for storing a characteristic of the laser diode; and
a second digital-analog converter electrically connected to the digital memory in such a way that the second digital-analog converter receives digital values read out from the digital memory and the second digital-analog converter converts the received values into the reference signal; the actuation and evaluation circuit further comprising:
a subtractor for subtracting the reference signal from the signal supplied by the photodiode which is electrically connected to the laser diode and the photodiode.

7. Method for measuring the concentration of a gas, comprising:
generating light in an absorption line of the gas;
measuring the light transmitted through a spatial region, wherein the gas is provided in the spatial region so that a transmission signal is generated
reading out a digital representation of a reference signal from a digital memory;
analog-converting the digital representation of the reference signal in a first digital-analog converter so as to obtain the reference signal
subtracting the reference signal from the transmission signal by an analog subtractor so as to obtain a difference signal.

8. Method according to claim 7, further characterized by:
adding in an analog manner a first constant offset to an analog output signal of a second digital-analog converter so as to obtain a driving signal for actuating a laser diode to generate the light.

9. Method according to claim 8, further characterized by:
providing the same digital values on the address lines to the digital memory and on the digital inputs of the second digital-analog converter.

10. Method according to claim 8, further characterized by:
generating a triangle signal by a microprocessor at the digital inputs of the second digital-analog converter.

11. Method according to claim 10, further characterized by:

Integrating the difference signal either over a period of the driving signal or the period from a minimum to a maximum of the driving signal or the period from a maximum to a minimum of the driving signal.

12. Method according to claim 9, further characterized by: generating a triangle signal by microprocessor at the digital inputs of the second digital-analog converter.

* * * * *